US00PP24753P3

(12) United States Plant Patent
Harris

(10) Patent No.: US PP24,753 P3
(45) Date of Patent: Aug. 12, 2014

(54) AZALEA PLANT NAMED 'MNIHAR022'

(50) Latin Name: ***Rhododendron* sp.**
Varietal Denomination: MNIHAR022

(76) Inventors: James O. Harris, Lawrenceville, GA (US); Ella Ruth Harris, legal representative, Lawrenceville, GA (US)

( * ) Notice: Subject to any disclaimer, the term of this patent is extended or adjusted under 35 U.S.C. 154(b) by 74 days.

(21) Appl. No.: 13/506,320

(22) Filed: Apr. 11, 2012

(65) Prior Publication Data

US 2013/0276186 P1 Oct. 17, 2013

(51) Int. Cl.
*A01H 5/00* (2006.01)

(52) U.S. Cl.
USPC ..... Plt./238

(58) Field of Classification Search
CPC ..... A01H 5/02
USPC ..... Plt./238, 240
See application file for complete search history.

*Primary Examiner* — June Hwu
(74) *Attorney, Agent, or Firm* — Jondle Plant Sciences Division of Swanson & Bratschun, L.L.C.

(57) ABSTRACT

A new and distinct variety of azalea plant with spring blooming, attractive, showy, single light pink with red border flowers, easily propagated by semi-hardwood cuttings in late spring through summer, moderate growth rate under normal fertilization and moisture conditions, compact broadly globose and freely branching in habit, grows well in containers, thrives in shade or sun and is hardy in Zone 6, is disclosed.

2 Drawing Sheets

Genus and species: *Rhododendron* sp.
Variety denomination: 'MNIHAR022'.

BACKGROUND OF THE NEW PLANT

The present invention is a new and distinct variety of evergreen azalea of the genus *Rhododendron*. This new azalea, hereinafter referred to as 'MNIHAR022', originated from a planned cross hybridization between the female azalea plant 'Fascination' (unpatented) and the male azalea plant 'Midnight Flare' (unpatented) in a controlled environment in Lawrenceville, Ga. in 2004. The present invention has a blooming period in April, a compact, broadly globose growth habit, and cold hardiness.

The new plant was first propagated via semi-hardwood cuttings in 2005 in Dearing, Ga. and has been asexually reproduced repeatedly by semi-hardwood cuttings in Dearing, Ga. for over 5 years and four generations. 'MNIHAR022' has been found to retain its distinctive characteristics through successive asexual propagations via semi-hardwood cuttings.

Plant Breeder's Rights for this variety have not been applied for. 'MNIHAR022' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Dearing, Ga.

1. Spring flowers;
2. Attractive, showy, light pink with red border flowers;
3. Numerous single flowers;
4. Easily propagated by semi-hardwood cuttings in late spring through summer;
5. Moderate growth rate under normal fertilization and moisture conditions;

6. Compact, broadly globose growth habit;
7. Grows well in containers;
8. Thrives in shade or sun; and
9. Hardy in Zone 6.

DESCRIPTION OF THE PHOTOGRAPHS

This new azalea variety is illustrated by the accompanying photographs. The colors shown are as true as can be reasonably obtained by conventional photographic means. The photographs are of five-year-old plants grown in filtered shade and full sun in 2010 and 2011 in Dearing, Ga.

DETAILED BOTANICAL DESCRIPTION OF THE NEW PLANT

Figure 1:
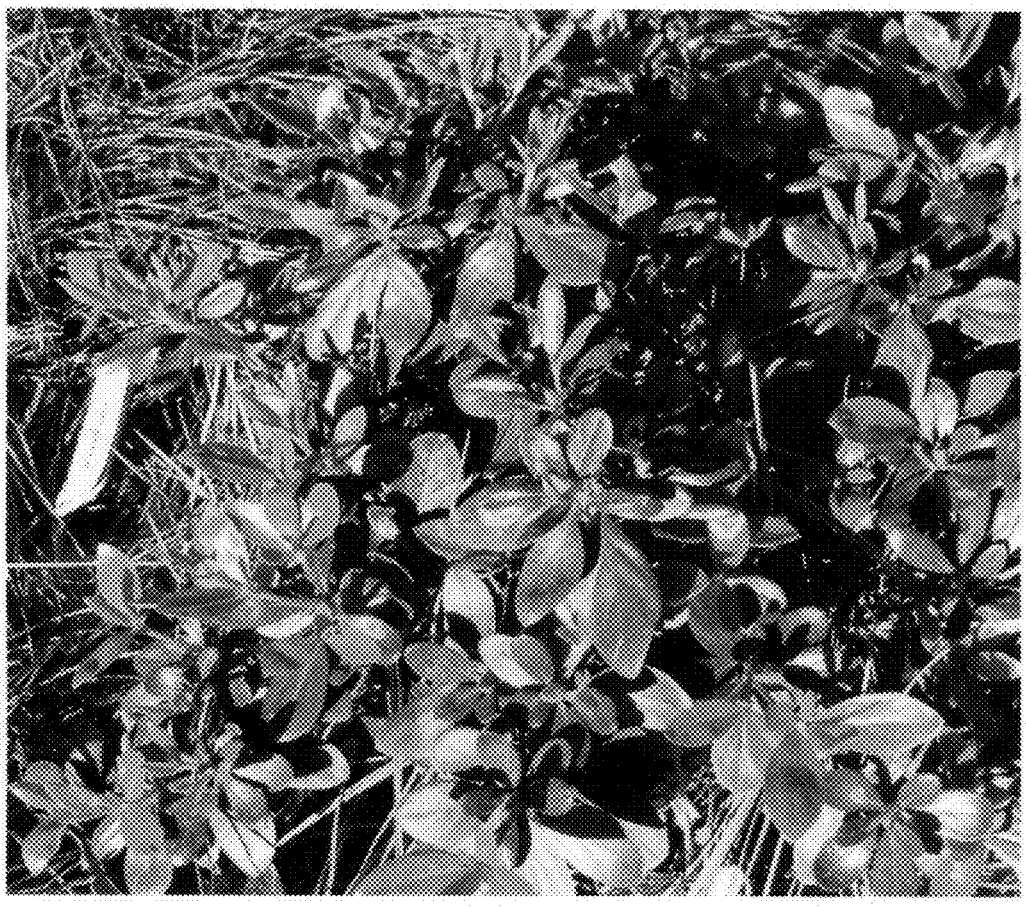
FIG. 1 is a close-up showing mature and immature foliage.
Figure 2:
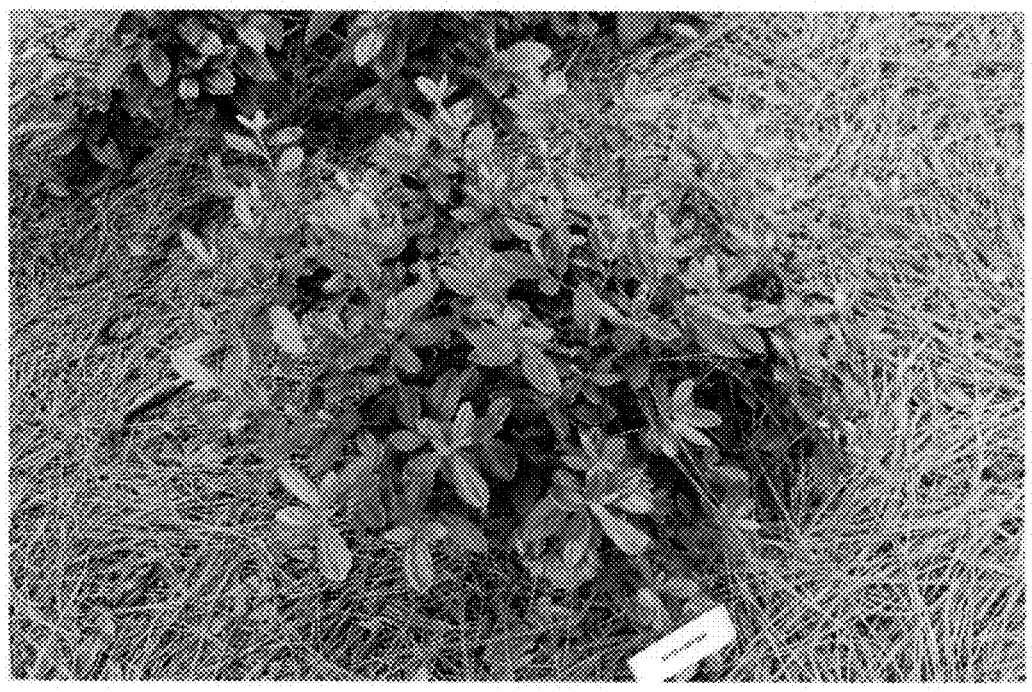
FIG. 2 shows mature foliage and growth habit of a five year old plant.
Figure 3:
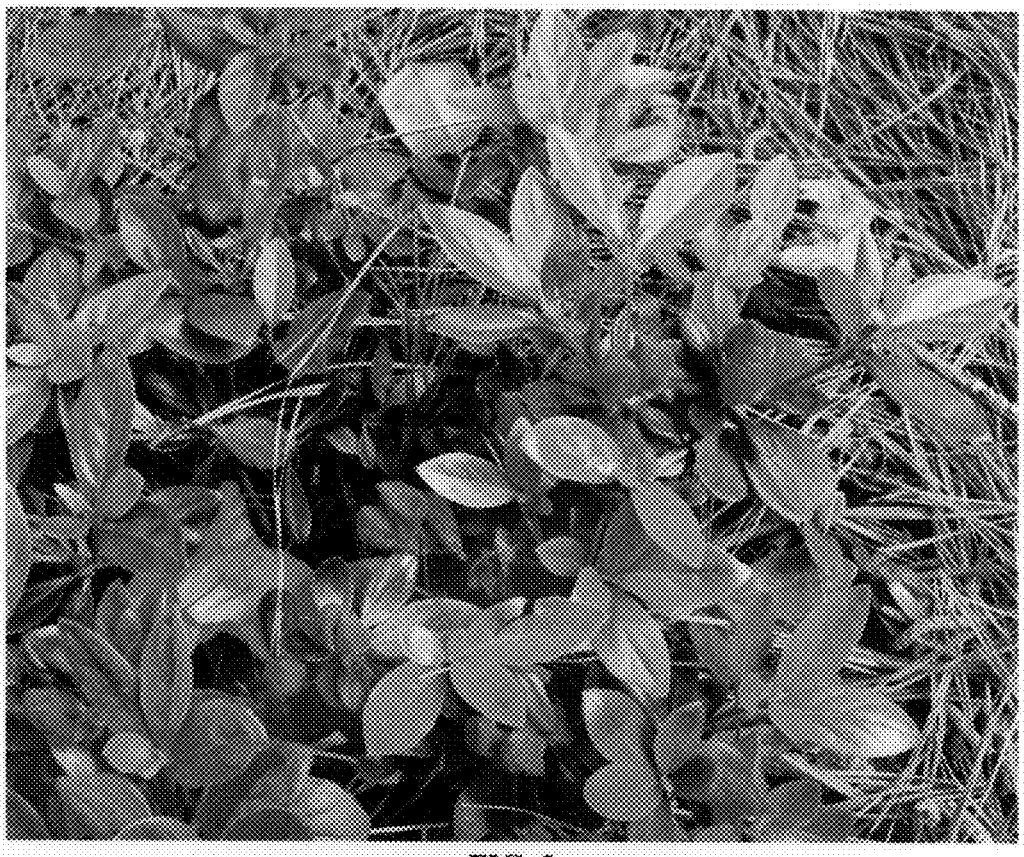
FIG. 3 is a close-up showing flower buds.
Figure 4:
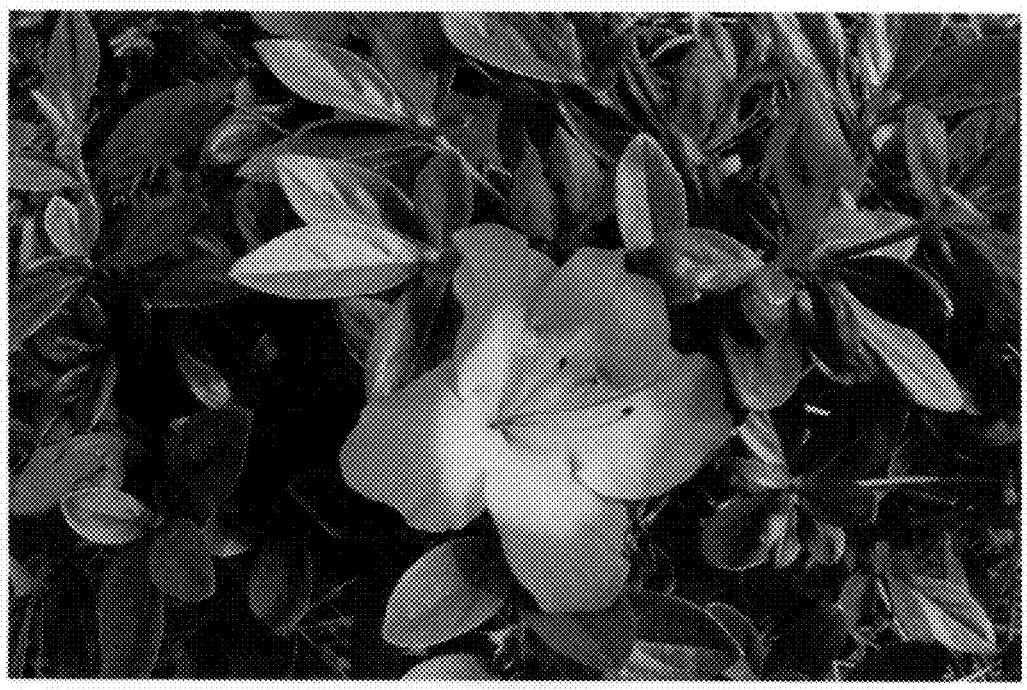
FIG. 4 is a close-up showing flower size, form, and color.

The following is a detailed description of the new variety of azalea based on observations made of five year old plants grown in ground in a part shade trial planting and three-year-old plants grown in trade and three-gallon containers according to wholesale commercial production conditions, under full-sun and in an evaluation bed under semi-shade conditions in Dearing, Ga. in the spring, summer, and fall seasons of 2009, 2010, and 2011. The colors of the various plant parts are detailed with reference to The Royal Horticultural Society Colour Chart (2001).

Classification:

*Family*.—Ericaceae.
*Species*.—*Rhododendron* sp.
*Common name*.—Azalea.
*Denomination*.—'MNIHAR022'.

Parentage:

*Female parent*.—The azalea plant 'Fascination' (unpatented).

*Male parent*.—The azalea plant 'Midnight Flare' (unpatented).

Plant:

*Form*.—Compact, dense, broadly globose.

*Texture*.—Medium.

*Height*.—60.96 cm to 91.44 cm.

*Width*.—91.44 cm to 121.92 cm.

*Growth habit*.—Freely branching; broadly globose and compact in nature.

*Growth rate*.—Moderate growth rate under normal fertilization and moisture conditions. In a period of 5 years from a rooted cutting the plant reaches a height of 28.0 cm and a spread of 60.0 cm. The growth rate is normally averages about 8.7 cm per year; the plant reaches a height of 60.96 cm to 91.44 cm at maturity while maintaining an compact, dense habit due to the abundant branch development.

*Spring growth*.—The date of initial spring growth is March 15, followed by continuous growth through fall.

*Life cycle*.—Perennial and evergreen.

Leaves:

*Arrangement*.—Alternate, simple, pubescent, and evergreen.

*Shape*.—Oblanceolate to elliptic.

*Apex*.—Mucronate.

*Base*.—Attenuate.

*Margin*.—Entire.

*Length*.—4.2 cm.

*Width*.—1.8 cm.

*Venation pattern*.—Pinnate; the mid-veins and laterals are impressed on the upper surface and the prominent on the lower surface.

*Immature leaf upper surface*.—Color: Semi-glossy, leaf emerges as RHS 144A (yellow-green) and becomes RHS 146A (yellow-green) once fully expanded, but still immature. Pubescence: lightly strigose. Pubescence color: RHS N155A (white) and RHS 164B (greyed-orange).

*Immature leaf lower surface*.—Color: Semi-glossy, leaf emerges as RHS 144A (yellow-green) and becomes RHS 146B (yellow-green) once fully expanded, but still immature. Pubescence: Strigose along the veins. Pubescence color: RHS N155A (white) and RHS 164B (greyed-orange). Mature leaf upper surface: Color: Glossy to Semi-glossy, RHS 139A (green). Pubescence: Small amount of strigose. Pubescence color: RHS 155C (white).

*Mature leaf lower surface*.—Color: Semi-glossy, RHS 147B (yellow-green). Pubescence: Small amount of strigose. Pubescence color: RHS 164B (greyed-orange).

*Petiole*.—Length: 0.4 cm. Diameter: 0.125 cm by 0.1 cm. Pubescence: Strigose. Length: 0.1 cm. Color: Immature: RHS N155D (white). Mature: RHS 166A (greyed-orange).

*Color*.—Immature: RHS 144B (yellow-green). Mature: RHS 146A (yellow-green).

Stems:

*Form*.—Branched at terminal buds and from some axillary buds at leaf nodes.

*Young stems* (*actively growing, less than one year old*).—Color: RHS 184A (greyed-purple), RHS 144A (yellow-green) maturing to RHS165B (greyed-orange). Pubescence: Strigose. Pubescence color: Begins RHS N155D (white) maturing to RHS 165B (greyed-orange). Length of fully elongated flush: 4.0 cm on average. Diameter: 0.15 cm.

*Mature stems* (*one year old and older*).—Color: RHS N199B (grey-brown). Pubescence: Strigose. Pubescence color: RHS 200A (brown). Length: 6.0 cm on average for a full year's growth. Diameter: 0.25 cm in second year. Pith: Solid and uniform. Internode length: 0.65 cm.

Flower buds:

*Arrangement and form*.—At terminal; borne in groups of one, two or three flowers per bud with one or two buds per terminal, buds sheathed by one or two modified leaf bracts.

*Bracts*.—Length: Average 1.6 cm. Width: 0.4 cm. Color: Lower surface RHS 147B (yellow-green) and upper surface RHS 139A (green).

*Shape*.—Ovate.

*Apex*.—Acute.

*Base*.—Rounded.

*Length* (*at tight bud*).—1.0 cm.

*Diameter* (*at tight bud*).—0.6 cm.

*Color* (*of scales*).—Immature: RHS 145B (yellow-green). Mature: RHS 144A (yellow-green) with areas of RHS N34A (orange-red).

*Texture*.—Matte; strigose pubescence.

*Pubescence color*.—RHS 165B (greyed-orange).

*Pedicel*.—Length: 0.6 cm at point bud begins to open. Diameter: 0.2 cm. Texture: Pubescent, strigose and pilose pubescence. Pubescence color: RHS 164D (greyed-orange).

*Color*.—RHS 145A (yellow-green) maturing to RHS N34A (orange-red).

Calyx:

*Calyx diameter*.—0.9 cm.

*Sepal length*.—0.3 cm.

*Sepal width*.—0.3 cm.

*Sepal quantity*.—5.

*Texture*.—Pubescent, sericeous and villous pubescence mainly along the margin. Pubescence color: RHS N155A (white).

*Color*.—RHS 144A (yellow-green).

Flowers:

*Type*.—Perfect, Single flowers.

*Shape*.—Open funnel-shaped.

*Flowering habit and period*.—Borne on the previous season's growth; two to three weeks beginning in early April in Dearing, Ga.

*Lastingness of flowers on the plant*.—4 to 5 days in the sun; 4 to 6 days in the shade.

*Fragrance*.—Absent.

*Diameter*.—8.5 cm.

*Depth*.—3.0 cm.

*Petals*.—Quantity per flower and arrangement: Five imbricate petals that are fused at the base and remain fused up to 2.0 cm from the base. Shape: Obovate. Apex: Rounded. Base: Fused. Margin: Entire, slightly wavy. Texture (both upper and lower surfaces): Glabrous. Length (of petals without spots): 5.2 cm. Width (of petals without spots): 3.3 cm. Length (of petals with spots): 5.0 cm. Width (of petals with spots): 3.0 cm. Color: Upper surface (with spots): One half of petal on apex end RHS 45A (red) with RHS 46A (red) spots, one half of petal nearest the center of the flower RHS 56A (red) with RHS 34C (orange-red) spots. Upper surface (without spots): One half of petal on apex end RHS 45A (red), one half of petal nearest the center of the flower RHS 56A (red). Lower surface: One half of petal on apex end RHS 45A (red), one half of petal nearest the center of the flower RHS 56A (red). Spots are not visible on the lower surface.

Reproductive parts:

*Pistil*.—Quantity and form: Single, non-petaloid. Length: 4.2 cm. Diameter: 0.075 cm.

*Stigma*.—Color: RHS 187C (greyed-purple). Diameter: 0.125 cm.

*Style color*.—RHS 53A (red).

*Ovary*.—Pubescent, pilose with 5 locules. Color: RHS N155A (white).

*Stamens*.—Quantity: 5 per flower; non-petaloid. Filament length: 4.1 cm. Filament width: 0.05 cm. Color: RHS 65B (red-purple).

*Anther*.—Length: 0.25 cm. Width: 0.075 cm. Color: RHS N77A (purple). Pollen: Abundant. Color: RHS 155B (white).

Fruit and seed: Observed.

*Maturity*.—The capsule matures in about 6 months in Dearing, Ga. and the fruit set is low and contains about 100 to 150 non-winged seeds.

*Capsule length*.—1.0 cm.

*Capsule width*.—0.5 cm.

*Capsule color*.—RHS 146A (yellow-green).

CULTURE

'MNIHAR022' grows well in a wide range of conditions and tolerates sun to shade. 'MNIHAR022' prefers moist, well-drained soil that is rich in organic matter and responds well to mulching and medium applications of fertilizer. 'MNIHAR022' does best in soil with a pH of 5.0 to 5.5 and is propagated with semi-hardwood cuttings in late spring through the summer. Azaleas root in five to six weeks with a high percentage of rooting (80% plus). Tissue culture is also an effective means of propagation for azaleas.

DISEASES AND INSECTS

Susceptible to lace bugs, root weevils, and spider mites. Fungal and bacterial pathogens have not been observed, but no resistance testing has been performed.

COMPARISON WITH PARENTAL AND COMMERCIAL VARIEITES

In Table 1, 'MNIHAR022' is compared to parental varieties 'Fascination' (unpatented) and 'Midnight Flare' (unpatented).

TABLE 1

| Characteristic | 'MNIHAR022' | 'Fascination' | 'Midnight Flare' |
|---|---|---|---|
| Plant Height (Mature) | 60.96 cm to 91.44 cm | 106.68 cm | 106.68 cm |
| Flower Diameter | 8.5 cm | 11.43 cm | 7.62 cm |
| Flower Form | Single | Single | Single |
| Flower Color | Light pink with red border | Light pink with red border | Deep red |
| Bloom Period | April | Mid-April to Late April | April |
| Hardy Zone | 6 | 6 | 6 |
| Stamen Number | 5 | 5 | 5 |
| Stamen Type | Non-petaloid | Non-petaloid | Non-petaloid |

When 'MNIHAR022' is compared to the commercial variety 'Roblen' (U.S. Plant Pat. No. 16,248), 'MNIHAR022' has an compact, broadly globose growth habit with a height of 28.0 cm and a spread of 60.0 cm in 5 years, while 'Roblen' has a height of 91.44 cm and a spread of 60.96 cm in six years. Additionally, 'MNIHAR022' produces light pink with red border flowers, while 'Roblen' has bright red flowers.

I claim:

1. A new variety of azalea plant named 'MNIHAR022' as herein shown and described.

* * * * *